(12) United States Patent
Abbas et al.

(10) Patent No.: US 9,416,377 B2
(45) Date of Patent: Aug. 16, 2016

(54) CELLULOLYTIC ENZYME ENHANCEMENT OF DRY GRIND CORN PROCESSING AND ETHANOL PRODUCTION

(71) Applicant: ARCHER DANIELS MIDLAND COMPANY, Decatur, IL (US)

(72) Inventors: Charles Abbas, Champaign, IL (US); Wu-Li Bao, Champaign, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/390,506

(22) PCT Filed: May 3, 2013

(86) PCT No.: PCT/US2013/039496
§ 371 (c)(1),
(2) Date: Oct. 3, 2014

(87) PCT Pub. No.: WO2013/166405
PCT Pub. Date: Nov. 7, 2013

(65) Prior Publication Data
US 2015/0118716 A1 Apr. 30, 2015

Related U.S. Application Data

(60) Provisional application No. 61/642,810, filed on May 4, 2012.

(51) Int. Cl.
| | | |
|---|---|---|
| C12P 7/14 | (2006.01) |
| C12P 7/06 | (2006.01) |
| C12P 7/10 | (2006.01) |
| C12N 9/42 | (2006.01) |
| C12P 19/02 | (2006.01) |
| C12P 19/14 | (2006.01) |

(52) U.S. Cl.
CPC .............. *C12P 7/14* (2013.01); *C12N 9/2434* (2013.01); *C12P 7/06* (2013.01); *C12P 7/10* (2013.01); *C12P 19/02* (2013.01); *C12P 19/14* (2013.01); *Y02E 50/16* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| | | |
|---|---|---|
| 2011/0124070 A1 | 5/2011 | Duan et al. |
| 2012/0270263 A9 | 10/2012 | Fish et al. |
| 2012/0276593 A1 | 11/2012 | Li et al. |

FOREIGN PATENT DOCUMENTS

| | | |
|---|---|---|
| WO | WO 02/38786 | 5/2002 |
| WO | WO2009148945 | * 12/2009 |
| WO | WO 2011/126897 A1 | 10/2011 |

OTHER PUBLICATIONS

Dien et al. "Improved Sugar Conversion and Ethanol Yield for Forage Sorghum (Sorghum bicolor L. Moench) Lines with Reduced Lignin Contents" Bioenerg. Res. (2009) 2:153-164.*
Zhao et al. "Biomass yield and changes in chemical composition of sweet sorghum cultivars grown for biofuel" Field Crops Research 111 (2009) 55-64.*
Juhasz et al. "Characterization of cellulases and hemicellulases produced by Trichoderma reesei on various carbon sources" Process Biochemistry 40 (2005) 3519-3525.*
Sigma-Aldrich "Enzymatic Assay of Arylamidase (EC 3.4.11.2)" 3pgs. Revised: Jul. 18, 1995.*
NC-IUBMB "Enzyme Nomenclature. Recommendations EC 3.4.11 Amino peptidases" 1 pg. accessed Jan. 11, 2016.*
Adav et al. "Quantitative Secretomic Analysis of Trichoderma reesei Strains Reveals Enzymatic Composition for Lignocellulosic Biomass Degradation" Molecular & Cellular Proteomics, 11, M111. 012419, published online on Feb. 20, 2012, 38 pgs.*
Ana Beatriz Henriques et al., Enhancing Water Removal from Whole Stillage by Enzyme Addition During Fermentation, Cereal Chem., Nov. 5, 2008, pp. 685-688, vol. 85, Issue No. 5.
Ana Beatriz Henriques et al., Reduction in energy usage during dry grind ethanol by enhanced enzymatic dewatering of whole stillage: Plant trial, process model, and economic analysis, Industrial Biotechnology, Aug. 2011, pp. 288-297, vol. 7, Issue No. 4.
Hui Wang et al., Effect of Low-Shear extrusion on Corn Fermentation and Oil Partition, Journal of Agriculture and Food Chemistry, Feb. 20, 2009, pp. 2302-2307, vol. 57.

* cited by examiner

*Primary Examiner* — Thane Underdahl
(74) *Attorney, Agent, or Firm* — Corey Crafton

(57) ABSTRACT

A method to increase ethanol production from a corn dry-mill process is described that comprises adding an enzyme preparation derived from *Trichoderma reesei* having cellulolytic activity to a saccharification process that includes conventional alpha amylase and glucoamylase. The addition of the cellulolytic enzyme decreases viscosity of the saccharified mash and can increase ethanol yield from a dry grind fermentation by as much as 10% or more. Specific characteristics are provided to show surprising and advantageous results of one particular preparation of cellulolytic enzymes from *T. reesei*.

11 Claims, 4 Drawing Sheets

Ethanol yield

CELLULOLYTIC ENZYME ENHANCEMENT OF DRY GRIND CORN PROCESSING AND ETHANOL PRODUCTION

CROSS REFERENCE TO RELATED APPLICATION[S]

This Application is a 35 U.S.C. §371 national phase entry of PCT application No. PCT/US2013/039496 filed May 3, 2013, which claims priority to U.S. Provisional Application No. 61/642,810 filed May 4, 2012.

BACKGROUND

Ethanol made by anaerobic fermentation of sugars by yeast is the major fuel product made from renewable resources in the United States and Brazil. In Brazil, the primary sugar is sucrose, which is readily extracted from sugar cane, one of the most abundant renewable crops grown in that country. In the United States the most abundant renewable crop is corn. The sugar used for the production of ethanol from corn is derived by hydrolysis of the starch contained in the corn endosperm to dextrose (i.e., glucose) which is obtained in a two-step process often called liquefaction and saccharification, whereby the corn starch gelatinized by heating followed by treatment with starch degrading enzymes, in particular $\alpha$-amylase and glucoamylase to yield glucose monomers and some maltose, with only trace amounts of higher molecular weight saccharides.

Broadly speaking, there are two types of corn processing operations employed in the United States to produce ethanol, commonly referred to as—wet milling and dry milling, the latter often merely called a "dry grind" process. In a classical wet milling operation the starch is highly purified relative to a dry grind process. In wet milling, the corn grain is "steeped" (typically for 22-50 hours at about 50° C.) in an aqueous solution often including small amounts of a mild sulfur acid compound such as sulfur dioxide, sulfuric acid or calcium sulfate which loosens the pericarp (bran) tissue from the interior endosperm and germ tissue. Following the grinding of the steeped corn, the endosperm and germ tissue are separated from each other and from the bran by various filtration and differential density separation techniques. The starch fraction contained in the endosperm is highly purified and therefore easily liquefied and saccharified into dextrose with a relatively low cost for enzyme usage. Ethanol production from an efficient wet milling operation is estimated to be about 2.65 gallons per bushel of corn, however, wet milling to separate corn into its constituent components requires a high cost of equipment and resources, which must be offset by production of higher value products than ethanol. Typically, corn oil is also extracted from the separated germ and a protein enriched product called corn gluten feed or corn gluten meal is extracted from the separated bran, resulting in yet another byproduct denoted "corn fiber" typically used in animal feed.

A conventional dry grind process is much simpler but produces fewer products. In a dry grind operation the grain is subject to grinding to form a coarse whole corn flour that contains exposed starch granules released from the endosperm. The liquification process involves heating the whole ground mixture, which first gelatinizes then ultimately ruptures the starch granules making the starch polymer accessible to acid and enzymatic hydrolysis. The entire crude liquefied mixture is added to form the fermentation media for ethanol production. In the most efficient dry grind processes, approximately 2.75 gallons of ethanol can be obtained per bushel of corn. Because of the relative simplicity of the process, dry grind ethanol production is much less costly from an equipment and resource utilization perspective than a wet milling process although ethanol is the only substantial product made.

Dry grind ethanol production is the most cost effective and efficient process for making ethanol from corn and prior to the present invention, was thought to have reached the maximum output of ethanol possible from crudely ground corn flour. The present invention surprisingly provides still further improvements on the efficiency of ethanol production from a dry grind process without incurring substantial costs or investments in new equipment.

SUMMARY

Described herein is surprising application of cellulolytic enzymes in a dry mill ethanol production process by use of particular cellulase preparations from *Trichoderma reesei* available from AB Enzymes (Darmstadt, Germany) in combination with conventional glucoamylase for simultaneous saccharification of the starch and fiber content of ground whole corn at an economic enzyme dosing in the range of 0.01% to 0.1% wt/wt (enzyme protein/mash solids).

Higher ethanol production was demonstrated in laboratory scale shake flask fermentation testing that showed an increase of ethanol titers representing an increase in yield in the range of about 4% to about 22% depending on enzyme dose, mash concentration (g solids/g solids plus liquid) and fermentation time. In a comparative test it was demonstrated that the *T. reesei* cellulolytic preparation from AB Enzymes yielded an increase in ethanol yield of 17.7%, 13.6% and 7.4% at 24, 36 and 44 hours of fermentation respectively, while the next best *T. reesei* cellulolytic preparation available from other manufacturers yielded an increase in titer of only 9.8%, 6.2% and 2.7% at the same respective time points with the same concentration of enzyme and mash.

In addition, it was surprisingly discovered that the *T. reesei* cellulolytic preparation form AB Enzymes could operate at very high mash solids concentrations of up to 40% and that the ethanol titer was most substantially improved at the higher mash concentrations—opposite to expectations. In one embodiment it was demonstrated that after 36 hours of fermentation the improvement in ethanol yield was 22.2% using mash at concentration of 36% w/w, which was substantially better than the improved yield of 4.4% obtained with the same enzyme preparation when fermented with the same mash at a concentration of 28% w/w.

Proof of concept for significant increase in ethanol yields by application of the AB Enzymes cellulase enzymes in a dry grind process was demonstrated in an industrial plant scale continuous corn dry milling process, where the ethanol yield were increased by 2.3% to 7.4% measured at the end of fermentation process of 40 hrs. Energy savings and water reduction were also achieved through the reduction of water and gas use in the process by at least 5%. The process also produced higher value DDGS having higher protein (5-6% increase) and lipid content and with reduced fiber content (>10% reduction).

DETAILED DESCRIPTION

Definitions

Figure 1:
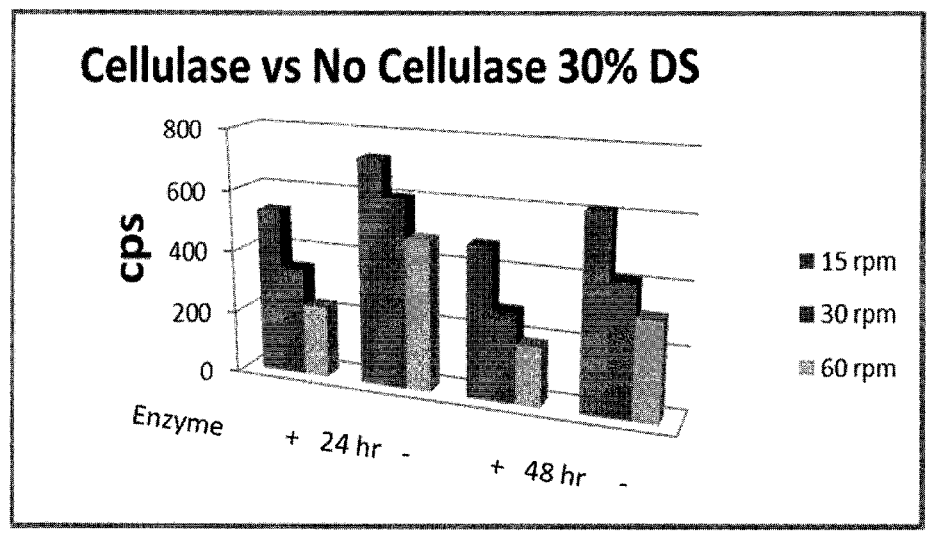
FIG. 1 is a chart showing the effect of a cellulolytic enzyme treatment using AB Enzymes cellulase preparation on the viscosity of a whole corn grain fermentation mash prepared by saccharification with glucoamylase.

For purposes of convenience and clarity, the following definitions are provided, which are believed to be consistent with the common meaning of terms as used in the art. If there is ambiguity between meaning asserted to be commonly understood and the definitions provided herein, the definitions herein provided are to control.

"Dry Grind" and "dry grind flour" means a process and the product thereof, whereby whole cereal grains, containing starch (endosperm), bran (pericarp) and germ (seed) tissue are ground to form a flour. It is understood that some water may be used to temper the grain before grinding or may be added after grinding, but the result is still a dry grind flour.

"Dry grind fermentation" and "dry grind ethanol fermentation" means use of a dry grind flour in a fermentation process to produce a fermentation product, such as ethanol. To operate as a dry grind fermentation, at least the starch present in the dry grind flour must be converted into sugars by a process of liquifaction and saccharification, the later including the use of at least one starch degrading enzyme such as glucoamylase and/or alpha-amylase. Optionally, a portion of some germ tissue or bran tissue may be separated prior to the liquification or saccharification, however at least 10% of the starting bran tissue must remain in the fermentation process to be considered a dry grind fermentation.

"Mash" is the liquefied and at least partially saccharified dry grind flour in water used as an input for a dry grind fermentation process.

"Cellulolytic enzyme(s)" refers to any protein or combination of proteins having an enzymatic activity capable hydrolyzing cellulose and/or hemicellulose and/or xylan polymers into digestible sugars. A comprehensive list and a source with references that describe these types of enzymes in more detail may be found, for example, in U.S. Provisional patent Application No. 61/538,211, which is incorporated herein by reference. Cellulolytic enzymes include blends containing any combination of any of the above types of enzymes.

"Cellulases" are a subclass of cellulolytic enzymes that include at least one enzyme with an activity defined as β-endoglucanases, cellobiohydrolases, β-glucosidases, or family 61 glucoside hydrolases.

"Hemicellulases" are a subclass of cellulolytic enzymes that include at least one enzyme with an activity defined as acetylmannan esterases, acetylxylan esterases, arabinasess, arabinofuranosidases, coumaric acid esterases, feruloyl esterases, galactosidases, glucuronidases, glucronoyl esterases, mannases, mannosidases, xylosidases or xylanases.

"Shake flask fermentation" is a fermentation process conducted in a laboratory where the fermentation media is present in a flask that is incubated in the presence of a fermentation organism (e.g, yeast) for time sufficient to form a fermentation product (e.g., ethanol). Shake flask fermentation is typically limited in volume to 12 gallons.

"Plant scale fermentation" is a fermentation process conducted in an industrial facility in a fermentation vessel containing at least 60,000 gallons of fermentation broth.

"Ethanol Yield" is a measurement of the amount of ethanol produced in a dry grind fermentation process related to the maximum amount of ethanol produced from the starch content of the mash on w/w basis as determined at a defined residence time in the fermentation.

"Ethanol Titer" is expressed alternatively as w/w, w/v, and v/v concentration of ethanol present in a fermentation media as determined at a defined residence time of fermentation.

"Solids content" of a mash (a.k.a "DS" for dissolved solids) is the percentage weight of solid material in a mash (excluding water and any added enzymes) divided by the total weight of the mash inclusive of water.

"Residence time" with respect to a fermentation process is the period of time a fermentation process is conduct before a fermentation product is harvested from the process. In a simple batch ethanol fermentation process where the fermentation process is started at time 0 and halted at time t to harvest the fermentation product from the broth, the residence time is the same as t. In a continuous ethanol fermentation process wherein a train of fermentation vessels are linked and continuously fed an input of mash or yeast at one or more input vessels while an output harvest of the fermentation broth containing the ethanol is withdrawn from another vessel in the train, the residence time is the average time a unit of mass is present in the fermentation train before harvest.

General

Ground corn used in dry grind ethanol fermentation contains starch, fat, protein and a lignocellulosic fibrous material in the bran) that consists primarily of hemicellulose, cellulose and lignin precursors present as esters of ferulic acid that are covalently linked to hemicellulose. It has been discovered that cellulolytic enzymes derived from the fungus *Tricoderma reesei*, which are commercially from manufacturers such as Novozymes (Franklinton, N.C.) Genencor/Danisco (Palo Alto, Calif.), AB Enzymes (Darmstadt, Germany) and Dyadic (Jupitor, Fla.), which were originally prepared for the purpose of digesting low-starch, high cellulose, high lignin content materials such as switch grass, corn stover, straw, wood and the like, when combined with glucoamylase, alpha amylase and/or other starch hydrolyzing enzymes, are also capable of enhancing the liquification, saccharification and physical properties of a mash prepared from a high-starch containing material such as dry grind corn flour and can lead to increases in ethanol yield.

Most surprisingly, however, it has been determined that not all commercial preparations of *T. reesei* cellulases significantly increase the yield of ethanol from fermentation of dry grind corn fermentation, and in particular, that the preparations made by AB Enzymes available under the trade name FLASHZYME® have superior properties that lead to a percentage increase in ethanol yields nearly twice and often more, the percentage increase increases obtainable by the next best preparation in a 36 hour fermentation.

Benefits of Combining Cellulolytic Enzymes with Starch Degrading Enzymes in Dry Grind Fermentation.

The treatment of dry grind corn flour with cellulolytic enzyme preparations from all manufactures appears to release more fermentable sugars from the corn flour than treatment with starch degrading enzymes alone.

A further benefit observed with treatment by all cellulolytic enzymes in combination with the starch degrading enzymes was that all reduced the viscosity of the fermentation mash, which in turn will reduce the amount of energy needed for agitation and mixing of the liquefied broth in an industrial operation.

Treatment with all cellulolytic enzymes also favorably impacted the separation by centrifugation of the fermentation mash after the fermentation, which would improve the evaporation of the backset (i.e., the water fraction remaining after distillation of ethanol from the fermentation broth). These benefits would result in modest energy savings for all dry grind ethanol processes enhanced by combination with any cellulolytic enzyme preparation.

Furthermore, the feed value of the residual mass remaining after fermentation was improved by saccharification that included cellulolytic enzyme treatment of dry grind corn. The information disclosed herein and supporting data can be of benefit to the whole corn and cereal dry mill ethanol industry which includes making ethanol for fuel, industrial and beverage uses.

The results described herein are based on a common process where whole ground corn was mixed with water and backset as done in a conventional dry grind ethanol plant to commence liquification of the starch in the ground corn with alpha-amylase (Liquozyme™ SC DS from Novozymes) at a dose of 0.2 g/kg mash solid to form a mash. The mixture of corn, water and backset with first dose of alpha amylase was heated and kept at 85° C. for 60 min, then heated to 108° C. and held at this temperature for 8 min. The mash was cooled down to 85° C. and more Liquozyme was added. After 3 hours the temperature was brought down to 30° C. Saccharification was commenced by the addition of glucoamylase (Spirizyme™ from Novozymes) at a dose of 0.1 g to 1.0 g/kg mash. The cellulolytic enzyme preparation from AB Enzymes (Darmstadt, Germany) was added at the dosage in the range of 1 to 10 g/kg of mash. Urea, glucoamylase, cellulase and yeast were added to start the fermentation.

Reduction of Viscosity in Fermentation.

Samples were taken at 24 and 48 hrs. of fermentation. Viscosity was measured at speeds of 15, 30 and 60 rpm with a #25 spindle using an LV-Brookfield viscometer. The viscosity of the cellulolytic enzyme treated fermentation broth over time is provided in FIG. 1 at different spindle speeds. The + refers to samples to which the cellulolytic enzyme product was added and control refers to the control samples without addition of the cellulase.

Better Centrifuge Separation.

At the end of the fermentation test, the broth was centrifuged to separate solids and the pellet size was measured. The pellet size % in Table 1 was the proportion of pellet size to the total volume of centrifuged broth. The pellet was collected and the moisture % was measured in an oven. From the table below, the pellet size was smaller in the cellulolytic enzyme treated fermentation broth than that of the control. The moisture content was also lower in the pellet from the enzyme treated broth.

TABLE 1

Effect of cellulase on the centrifugation process

|  | Cellulase treated | No enzyme control |
|---|---|---|
| pellet size % | 35% | 41% |
| pellet moisture % | 59% | 63% |

Higher Ethanol Yield

Figure 2:
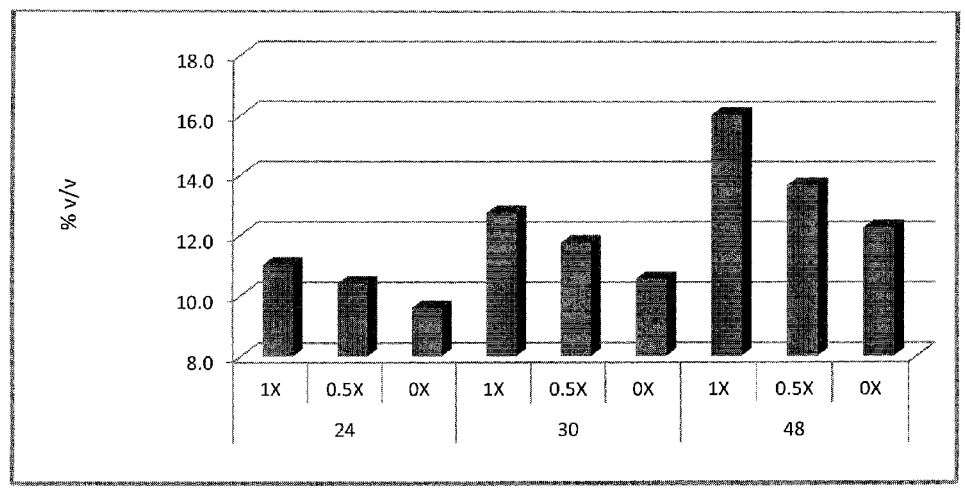
FIG. 2 is a chart showing the effect on ethanol titers from a batch fermentation process that included saccharification with glucoamylase in comparison to the same treatment supplemented with various amounts of AB Enzymes cellulase preparation. Enzyme dose

A laboratory scale batch fermentation was conducted to compare ethanol yields from ordinary glucoamylase saccharified dry grind and the same supplemented with the cellulolytic enzyme. Samples were taken at 24, 30 and 48 hrs of fermentation. Experiments were carried out with two enzyme dosage levels 1× (0.5 g enzyme protein/kg mash solid) and 0.5× (0.25 g enzyme protein/kg mash solid) and the results are illustrated in FIG. 2. Higher ethanol titers were demonstrated in the fermentation for both cellulolytic enzyme levels at 0.5× or 1× loading in comparison to the control (0×).

Better Feed Properties.

After fermentation, the resulting mash was sent for feed value analysis. At 0.5× and 1× cellulase loading, more protein, fat, total digestible nutrients and digestible energy (DE) are shown in the feed value analysis table comparing to that of the control (0×). The results also indicate that there was less fiber content (ADF acid detergent fiber and NDF neutral detergent fiber) in the enzyme treated mash after fermentation. These results are presented in Table 2.

TABLE 2

Feed value analysis of dry mill fermentation residues

| Sample ID | Cellulase dosage | protein | NDF | ADF | NFC | TDN | DE |
|---|---|---|---|---|---|---|---|
| 5426-8-1 | 0X | 33.1 | 43.7 | 15.3 | 13.9 | 80 | 1.34 |
| 5426-8-2 | 0.50X | 39.1 | 33.4 | 11.4 | 15.6 | 83 | 1.44 |
| 5426-8-3 | 1X | 38.3 | 32.9 | 12.2 | 16.8 | 83 | 1.45 |

Higher Ethanol Titer in a Continuous Fermentation Process

Figure 3:
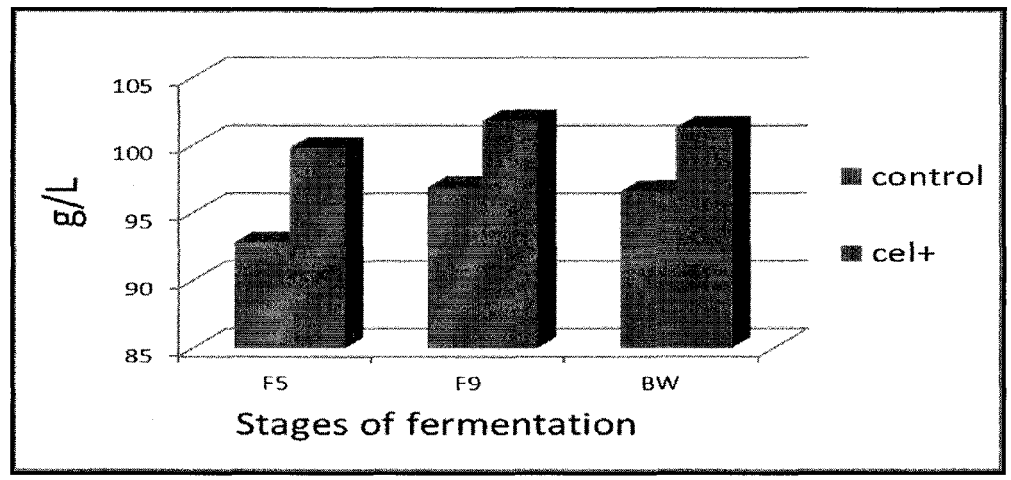
FIG. 3 is a chart showing increased ethanol production from a continuous laboratory scale fermentation process using a chain of fermenter vessels that included mash prepared by saccharification with glucoamylase (control) in comparison to the same treatment supplemented with various amounts of AB Enzymes cellulase preparation (cel+).

Preparation, liquefaction and saccharification of ground corn were carried out using the same methods as described above. A lab scale continuous cascade train consisting of nine fermentors (F1-F9) was set up for the ethanol fermentation. The yeast, glucoamylase and cellulase were added into the corn prepared mash at fermentor F1, then the fermentation broth was moved with a gradual gravity flow through F2 to F9 and the fermentation broth was collected in a beer well after F9. The flow rate was adjusted to insure a fermentation residence time of 45 hr with temperature controlled at 30° C. Samples were taken from the beer well and different fermentors and assayed for sugar, ethanol and co-products. FIG. 3 is a bar graph showing beer well ethanol titer at two different stages of the fermentation with Cel+ referring to the mash with cellulase added versus the control mash with no cellulase addition. Higher ethanol titer was observed when cellulase was added into the fermentation mash. F5 refers to fermenter vessel number 5 with an estimated residence time of 23 hrs and F9 refers to fermenter vessel number 9 with an estimated residence time of 45 hrs Plant Trial with Cellulase:

A set of six ethanol production scale fermenters (300,000 gallons each) were used in the trial. The fermentation was carried out in an agitated batch fermenter with temperature controlled at 34° C. The mash had a dextrose equivalent (DE) of about 12 and contained 30% solid at starting pH of 4.5. Dextrose equivalent or (DE) is a measure of the amount of reducing sugars present in a sugar product, relative to glucose, expressed as a percentage on a dry basis. After fermentation, the mash goes through a distillation process and the still bottoms are centrifuged to separate the cake from the supernatant (backset), which was concentrated by evaporation. The cake, together with the evaporated concentrate of the supernatant, were combined and dried in a rotary drier to make Distillers Dried Grains with solubles (DDGS). Ethanol and carbohydrate residues were measured at the end of fermentation and the cake was checked for solid content. During the production plant trial, a series of non-enzyme treated control fermentations were carried out before and after the trial period. Different enzyme dosages were tested in the trial (trial 1=0.025% protein/DS), trial 2=0.05% protein/DS and trial 3=0.1% protein/DS).

Figure 4:
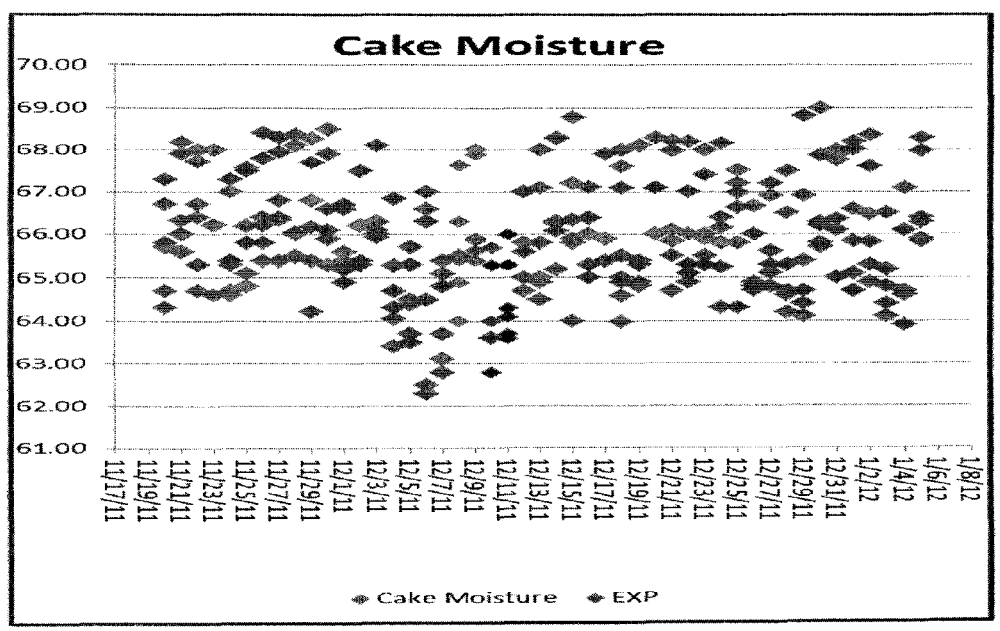
FIG. 4 is chart demonstrating improvement in solids separation (i.e., obtaining lower moisture content cakes) prepared by centrifugation of broth obtained after ethanol production and distillation from a conventional glucoamylase prepared mash from a corn dry grind (blue diamonds) in comparison to the same mash enhanced by treatment with AB Enzymes cellulase preparation (red diamonds).

During the 10 day trial, higher ethanol titers were observed for the fermentation batches that included test cellulase when compared to the controls (Table 3). Samples of centrifuged cake consistently had less moisture in the test fermenters that included cellulases (FIG. 4). Overall, less energy was necessary to dry the DDGS from the cellulase treated runs in comparison to control fermentations. Feed value analysis of the DDGS showed similar properties as to these observed in the laboratory scale experiments.

TABLE 3

Plant trial ethanol titer: 2 to 6% higher titers in presence of cellulolytic enzymes from AB Enzyme

| tests | ethanol titer v/v | % increase over control |
|---|---|---|
| controls | 15.2 | |
| Trial 1 | 15.6 | 2.6 |
| Trial 2 | 15.9 | 4.6 |
| Trial 3 | 16.1 | 5.9 |

Higher Solids Content of the Mash

Another surprising and long sought feature provided by the methods described herein, is the discovery that use of the cellulolytic enzyme preparations from AB Enzymes permits the mash to be prepared at higher solids content than mash prepared using only glucoamylase and alpha amylase. In ordinary dry grind fermentation using a conventional mash, when the solids content exceeds 30% the enzymatic activity of the amylases begins to stall relative to the amount of solids resulting in an upper limit on the final ethanol yield that can be obtained. It is therefore a waste to add any additional solids to increase the solids concentration of the mash because such addition results in a waste of materials. However, in a shake flask experiment using various concentrations of mash it was discovered that the mash concentration can be increased to at least 36% and probably could be increased to at least 40% with no loss of yield. The ground corn mixture containing 40% solid was liquefied with an alpha-amylase to make a mash using a method described earlier. The solid of the mash was adjusted to the levels listed in Table 4. After adjusting of pH and cooling to 30 C, 500 ppm urea was added to the liquefied mash. Glucoamylase Spirizyme was added at a dose recommended by the manufacture. Ethanol Red Yeast (Fermentis, USA) was pitched at a rate of 30 million cells/ml mash. To each flask, 130 gram of mash was added and AB Enzymes cellulase was added at a dose of 0.5 gram protein/kg of solid. The flasks were incubated in a shaker at 30 C and 150 rpm. The results are shown in Table 4.

TABLE 4

Effect of cellulase on different levels of fermentation solid

| mash solid | cellulase addition | 12 hr g/kg | 24 hr g/kg | 36 hr g/kg | % yield | % of control |
|---|---|---|---|---|---|---|
| 28% | yes | 51.2 | 81.2 | 95.7 | 87 | 4.4 |
|  | no | 41.8 | 70.6 | 91.7 | 83.4 |  |
| 30% | yes | 54 | 85.8 | 103 | 87.3 | 5.5 |
|  | no | 45.3 | 75.6 | 97.7 | 82.8 |  |
| 32% | yes | 57 | 90.9 | 110.1 | 88.1 | 13.9 |
|  | no | 45.8 | 76.1 | 96.7 | 77.4 |  |
| 34% | yes | 58 | 95.5 | 117.8 | 87.9 | 17.4 |
|  | no | 48 | 79.1 | 100.4 | 74.9 |  |
| 36% | yes | 59.8 | 101.5 | 126.5 | 89.7 | 22.2 |
|  | no | 49.9 | 81.7 | 103.7 | 73.5 |  |

It will be noted that in the absence of the cellulolytic enzyme the ethanol yields from the mash did not improve markedly when the mash solids content exceeded 30% but in the presence of the cellulolytic enzymes, the ethanol yields continued to improve, showing at least up to a 22.2% improvement at the highest tested mash solids content of 36%. It is believe that mash solids contents as high as 40% will also be useable.

Figure 5:
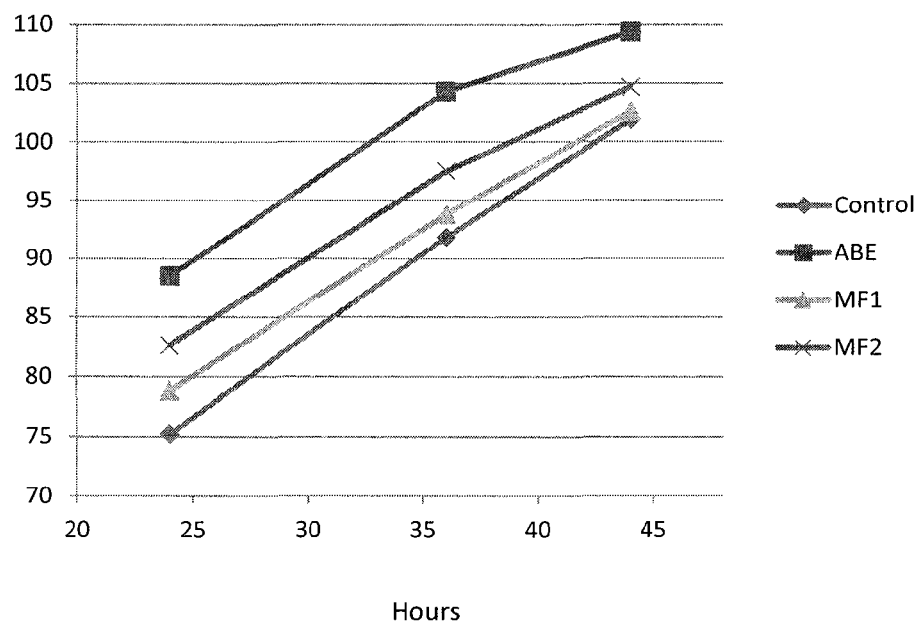
FIG. 5 is a graph showing ethanol yields (expressed as g ethanol per kg broth) obtained using the cellulolytic preparations from AB Enzymes (ABE) in comparison to two other cellulolytic enzyme preparations derived from *T. reesei* obtained from two other manufacturers (MF1 and MF2).

The foregoing results were obtained using the *T. reesei* cellulolytic enzyme preparation obtained from AB Enzymes. In seeking to compare other *T. reesei* cellulolytic enzyme preparations available from other manufactures it was surprisingly discovered that no other preparation performed as well in terms of enhancing ethanol yield. In a comparative 250 ml shake flask study conducted over a 44 hour period using 150 g of mash having a solids content of 30% the AB Enzymes preparation (ABE) consistently demonstrated nearly two fold better performance in terms of improvement in ethanol yields in comparison to the cellulolytic enzyme preparations form other manufactures herein designated "MF1" and "MF2". In all cases preparation of the mash included the same amounts of identical glucoamylase and alpha amylases, and identical protein amounts of the cellulolytic enzyme preparations, at a dose of 0.5 g enzyme protein/kg mash solid from the different manufacturers, or no cellulolytic enzymes as a control. The results of the comparison are shown in Table 5 below and graphically illustrated in FIG. 5.

TABLE 5

Comparative ethanol titers in w/w at different fermentation times with different cellulolytic preparations with 150 g mash

| | 24 hr. | % better than control | 36 hr. | % better than control | 44 hr. | % better than control |
|---|---|---|---|---|---|---|
| No enzyme ctrl | 75.2 | 0 | 91.8 | 0 | 101.9 | 0 |
| ABE | 88.5 | 17.7% | 104.3 | 13.6 | 109.4 | 7.4 |
| MF1 | 78.8 | 4.8% | 93.8 | 2.2 | 102.6 | 0.7 |
| MF2 | 82.6 | 9.8% | 97.5 | 6.2 | 104.7 | 2.7 |

Figure 6:
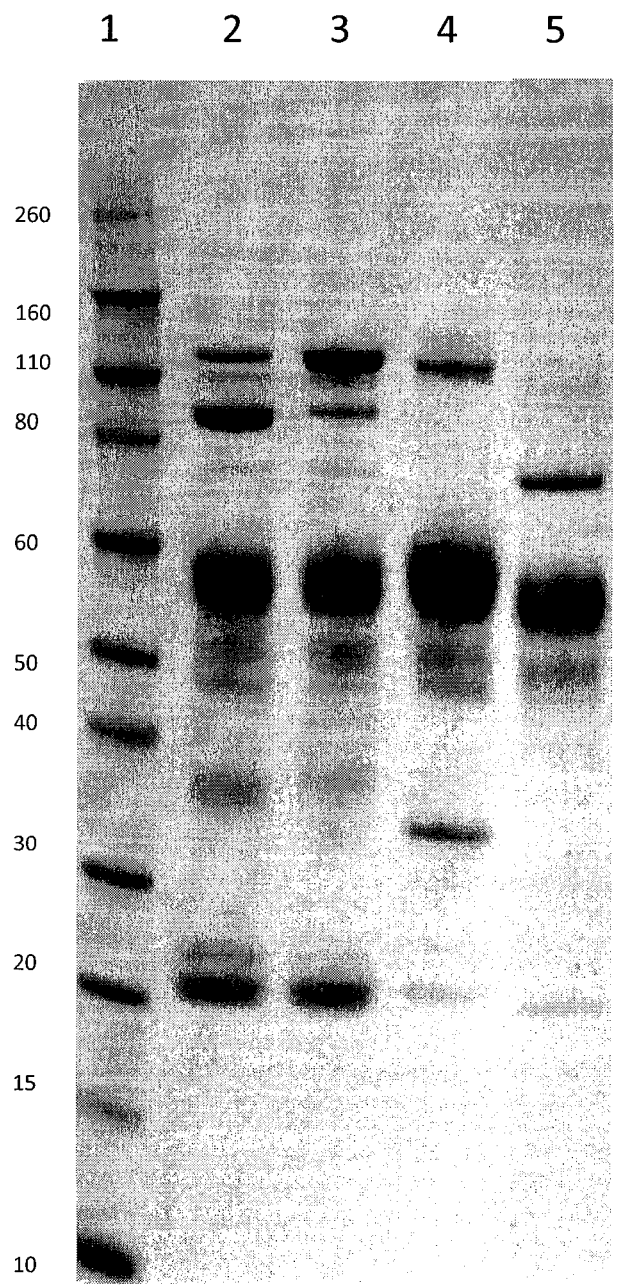
FIG. 6 depicts a Coomassie stained 10% SDS polyacrylamide gel showing the differences in protein bands present in various commercial preparations of *T. reesei* cellulolytic enzymes obtained from AB Enzymes (lane 4), MF1 (lanes 5) and from MF2 (lanes 2 and 3). Molecular weight markers are shown in lane 1.

Although each of the enzyme preparations were derived from *T. reesei*, the preparation from AB Enzymes shows four distinguishing characteristics when analyzed by 10% SDS polyacrylamide gel electrophoresis shown in FIG. 6. Molecular weight markers are shown in lane 1. Equal amounts of protein from various commercial preparations are shown in lanes 2-5. Two different commercially available preparations obtained from MF2 are shown in lanes 2 and 3. The commercial preparation from AB Enzymes is shown in lane 4. The commercial preparation obtained from MF1 is shown in lane 5.

All preparations exhibited a dominant band corresponding to a molecular weight of about 56-58 kd and a second less dominant band corresponding to a molecular weight of about 115-130 kd. Scanning the density of the bands in the gel reveals that for the AB Enzymes preparation this second band was present at no more than 7.5% to 15% the intensity of the dominant band. In the other preparations this second band was present in greater proportions relative to the dominant band. In addition, the AB enzymes preparation has a third band corresponding to a molecular weight of about 32-36 kd that is also about 7.5% to 15% the intensity of the dominant band. The other preparations lack this band altogether, or at least less than the limit of detectability by coomassie staining. For clarity in understanding, the limit of detectability in this analysis is about 1% of the intensity of the dominant band at 56-58 kd.

Furthermore, the AB Enzymes preparation is distinguishable by a lack of other proteins that are present in the other preparations. In particular, the AB Enzymes preparation is also characterized as having no bands corresponding to a molecular weight of between 10 kd to 32-36 kd that is more than 5% the intensity of the dominant band at 56-58 kd. The preparations from MF2 each have at least one major band in this range of much higher intensity. Finally the AB Enzymes preparation is distinguishable by having no bands corresponding to a molecular weight between the molecular weight of the dominant band of 54-56 kd and the second band at about 155-130 kd that is more than 5% the intensity of the dominant band at 56-58 kd. The preparations from each of the other manufacturers display one or more bands in this size range with greater intensity.

The cellulolytic enzyme preparation from AB Enzymes also may be distinguishable by displaying different amounts and ratios of measurable hydrolytic activities. A commercially available semi-quantitative enzyme activity assay kit API Zym (bioMérieux, Inc. Durham, N.C. 27712) provided a way to indicate the presence of a variety of distinguishable hydrolytic activities by specific chromogenic colorations, which provides a semi-quantitative assessment of the relative levels of certain specific activities that may be present in different samples. The assays are based relative color observed for the various activities on a relative scale of 1-10. The AB Enzymes cellulolytic preparation was compared against the preparations from MF1 and MF2 using this kit, and the results are shown in Table 6.

TABLE 6

Relative enzymatic activities in Cellulolytic Enzyme Preparations

| | Enzymes | MF1 | ABE | MF2 |
|---|---|---|---|---|
| 1 | Control | 0 | 0 | 0 |
| 2 | alkaline phosphatase | 5 | 6 | 6 |
| 3 | Esterase | 4 | 5 | 5 |
| 4 | esterase lipase | 3 | 5 | 5 |
| 5 | Lipase | 1 | 1 | 1 |
| 6 | leucine arylamidase | 0 | 1 | 1 |
| 7 | valine arylamidase | 0 | 3 | 1 |
| 8 | cystine arylamidase | 1 | 3 | 0 |
| 9 | Trypsin | 2 | 3 | 2 |
| 10 | Chymotrypsin | 1 | 2 | 2 |
| 11 | acid phosphatase | 5 | 5 | 5 |
| 12 | Phosphohydrolase | 8 | 8 | 8 |
| 13 | α-galactosidase | 5 | 5 | 5 |
| 14 | β-glucuronidase | 5 | 5 | 5 |
| 15 | β-glucunronidase | 3 | 3 | 3 |
| 16 | α-glucosidase | 2 | 5 | 5 |
| 17 | β-glucosidase | 2 | 6 | 6 |
| 18 | acetyl glucosaminidase | 5 | 5 | 6 |
| 19 | α-mannosidase | 0 | 3 | 1 |
| 20 | α-fucosidase | 0 | 1 | 1 |

The most notable feature of the comparison shown in Table 6 is that the AB Enzymes cellulolytic enzyme preparations contains higher levels of the proteases valine arylamidase, cystine arylamidase and trypsin. While not being bound by theory, it is believed that when using cellulolytic enzymes in the manner taught herein to improve ethanol yield from dry grind fermentation, some optimal level of protease activity is preferred to be present. The presence of some protease is desirable to loosen proteins and peptidyl glycans that may be intertwined or bound to cellulose and hemicellulose present in the mash, making these polysaccharides more accessible to the cellulase and hemicellulase activities. Too little protease will therefore not provide the best release of sugars from these carbohydrates. On the other hand, too much protease activity will cause unwanted digestion of the very cellulolytic enzymes needed to digest these carbohydrates.

Another distinguishing feature of the AB Enzymes preparation is the specific activity levels of certain specific hydrolytic activities is higher, and certain ratios of specific activities differ. Table 7 shows a comparison of the specific activities measured in the ABE Enzymes preparation in comparison to other preparations.

TABLE 7

Specific Hydrolytic Activities of *T. Reesi* cellulolytic enzyme preparations
(expressed as units per mg protein in the preparation)

| Source | PCU/mg * | CBHI/mg * | EGI/mg * | ECU/mg * | BGU/mg * | BXU/mg * | Ratio ECU/PCU | Ratio BXU/ECU |
|---|---|---|---|---|---|---|---|---|
| MF1 | 17.1 | 10.8 | 6.3 | 394.5 | 156.1 | n.a. | 23.03 | n.a. |
| MF2a | 10.4 | 6.7 | 3.7 | 222.7 | 567.5 | 1741.6 | 21.48 | 7.82 |

TABLE 7-continued

Specific Hydrolytic Activities of *T. Reesi* cellulolytic enzyme preparations
(expressed as units per mg protein in the preparation)

| Source | PCU/mg * | CBHI/mg * | EGI/mg * | ECU/mg * | BGU/mg * | BXU/mg * | Ratio ECU/PCU | Ratio BXU/ECU |
|---|---|---|---|---|---|---|---|---|
| MF2b | 15.9 | 11.0 | 4.9 | 213.7 | 168.5 | 57.9 | 13.47 | 0.27 |
| ABE | 23.6 | 17.3 | 5.5 | 280.3 | 635.9 | 585.2 | 11.85 | 2.09 |

The activities reported in Table 7 are as follows: PCU is a combined cellulase activity defined hereafter; CBH is cellobiohydrolase, EGI is endoglucanase I; ECU is total endogluanase; BGU s beta-glucosidase; and BXY is xylanase activity.

PCU activity is a joint activity of cellobiohydrolases and endoglucanase I. Measurement of PCU activity has been previously described as detailed in WO2008080495. Briefly, .Beta-glucosidase activity in the sample is suppressed by 100 mM glucose in the reaction mixture. A PCU unit is defined as the amount of enzyme activity that releases 1 nmol 4-methylumbelliferone from 4-methylumbelliferyl-β-D-galactoside per second under the experimental conditions (pH 5.0, 50° C., 10 min incubation).

The proportion of the different enzymes cellobiohydrolase and endoglucanse can be measured individually by the addition of 5 mM cellobiose in the reaction mixture, whereby the reaction of the CBH with is defined as the amount of enzyme producing one nmole of reducing sugars as glucose in one second All solutions are prepared in deionized water, Milli-Q or equivalent. The assay uses 50 mM sodium citrate buffer pH 4.8. The substrate is prepared by dissolving 1.00 g hydroxyethyl cellulose (2-hydroxyethyl-cellulose) in 100 ml of sodium citrate buffer. The detection reagent DNS i is prepared by dissolving 50.0 g of 3,5-dinitrosalicylic acid in about 4 l of water. A typical is performed by adding 1.8 ml of substrate solution to each of two test tubes that are then equilibrated at 50° C. for 5 min. Then 200 µl of diluted sample solution is added to initiate the reaction. After 10 min incubation, 3.0 ml of DNS reagent is added and the reaction halted by boiling in water bath for 5 minutes. Activity is determined by measuring the absorbance against a blank at 540 nm referenced from a standard curve.

Four different preparations of the AB Enzymes preparation were evaluated although the only one reported in the table is the same as that used in the experiments outlined in this disclosure. For all preparations, however, case there were several features that particularly distinguished the AB Enzymes preparation from other preparations. First the ABE preparation has a PCU activity of at least 20 units/mg, which was at least 40% higher than the PCU specific activity of other preparations. Second, the AB Enzymes preparations all had a CBH specific activity of at least 14 units per mg, which is at least 27% higher than all other preparations tested. Lastly, and perhaps most critically, the ratio of PCU/ECU activity in the all the AB Enzymes preparation was consistently between 10 and 13. The PCU/ECU activities in all other samples was always over 13 and as high as 24.

Accordingly, it is believed that the AB Enzymes preparation can be defined in several ways that distinguish this type of cellulolytic enzyme preparation over other preparations available in the art. Namely, by the higher yield of ethanol that may be obtained from an dry grind ethanol fermentation using the preparation; by the distinctiveness of the banding pattern displayed on an SDS polyacrylamide gel, by the presence of proteases, and by certain minimum specific activities for PCU and CBH and ratio of activities of PCU to ECU as demonstrated above and recited in the claims that follow.

What is claimed is:

1. A method of making ethanol by fermentation of a ground whole grain product, comprising
    in a water mixture, contacting the ground whole grain product with a starch degrading enzyme and a cellulolytic enzyme preparation from *Trichoderma reesei* for a time sufficient to hydrolyze at least a portion of starch, cellulose and hemicellulose in the flour into fermentable sugars, forming an enhanced mash, wherein said cellulolytic enzyme preparation exhibits a combined cellobiohydralase (CBHI/mg) and endogluconase I (EGI/mg) activity (collectively, PCU activity) of at least 20 Units/mg when measured at pH 5.0 at 50° C. for 10 minutes; wherein said cellulolytic enzyme preparation exhibits each of alkaline phosphatase, esterase, esterase lipase, lipase, leucine arylamidase, valine arylamidase, cystine arylamidase, trypsin, chymotrypsin, acid phosphatase, phosphohydrolase, alpha galactosidase, beta galactosidase, beta glucuronidase, alpha glucosidase, beta glucosidase, acetyl glucosaminidase, alpha mannosidase and alpha fucosidase activities; and
    fermenting the enhanced mash to produce ethanol, wherein an achieved yield of ethanol from the enhanced mash expressed as weight ethanol/weight solids content of the enhanced mash after 40 hours of an industrial plant scale fermentation is 2.3-7.4% greater than a comparative yield of ethanol made by fermenting a comparative mash made by an identical process as the enhanced mash and having the same solids content the enhanced mash, but that was not contacted with the cellulolytic enzyme preparation.

2. The method of claim 1 wherein the solids content of the mash is about 32-40%.

3. The method of claim 1 wherein contacting with the cellulolytic enzyme preparation occurs prior to contacting with the starch degrading enzyme.

4. The method of claim 1 wherein contacting with the cellulolytic enzyme preparation occurs after contacting with the starch degrading enzyme.

5. The method of claim 1 wherein contacting with the cellulolytic enzyme preparation occurs simultaneously with contacting with the starch degrading enzyme.

6. The method of claim 1 wherein contacting with the cellulolytic enzyme preparation occurs simultaneously with the fermenting.

7. The method of claim 1 wherein said cellulolytic enzyme preparation further exhibits a total endoglucanase activity (ECU activity) and a ratio of PCU to ECU activity that is 10-13.

8. The method of claim 1 wherein the ground whole grain product is ground corn grain.

9. A method of making ethanol by fermentation of a ground whole grain product, comprising in a water mixture, contacting the ground whole grain product with a starch degrading enzyme and a cellulolytic enzyme preparation from *Trichoderma reesei* for a time sufficient to hydrolyze at least a portion of starch, cellulose and hemicellulose in the flour into fermentable sugars, forming an enhanced mash, wherein said cellulolytic enzyme preparation exhibits a combined cellobiohydralase and endogluconase I activity (collectively, PCU activity) of at least 20 Units/mg when measured at pH 5.0 at 50° C. for 10 minutes; wherein said cellulolytic enzyme preparation exhibits each of alkaline phosphatase, esterase, esterase lipase, lipase, leucine arylamidase, valine arylamidase, cystine arylamidase, trypsin, chymotrypsin, acid phosphatase, phosphohydrolase, alpha galactosidase, beta galactosidase, beta glucuronidase, alpha glucosidase, beta glucosidase, acetyl glucosaminidase, alpha mannosidase and alpha fucosidase activities; and fermenting the enhanced mash to produce ethanol, wherein an achieved yield of ethanol from the enhanced mash expressed as weight ethanol/weight solids content of the enhanced mash after a lab scale shake flask fermentation residence time of 24 to 44 hours is at least 5% greater than a comparative yield of ethanol made by fermenting a comparative mash made by an identical process as the enhanced mash and having the same solids content the enhanced mash, but that was not contacted with the cellulolytic enzyme preparation.

10. The method of claim 9 wherein the solids content of the mash is at 34% to 40% and the achieved yield of ethanol that would be measured at a residence time of 36 hours is at least 15% greater than the comparative yield of ethanol.

11. The method of claim 9 wherein the solids content of the mash is about 36% and the achieved yield of ethanol that would be measured at a residence time of 36 hours is at least 20% greater than the comparative yield of ethanol.

* * * * *